United States Patent [19]

Robyt et al.

[11] 4,335,100
[45] Jun. 15, 1982

[54] METHOD OF INHIBITING DEXTRANSUCRASE AND ORAL COMPOSITIONS FOR USE THEREIN

[75] Inventors: John F. Robyt, Ames, Iowa; John N. Zikopoulos, Phoenix, Ariz.

[73] Assignee: Iowa State University Research Foundation, Inc., Ames, Iowa

[21] Appl. No.: 175,635

[22] Filed: Aug. 6, 1980

Related U.S. Application Data

[63] Continuation-in-part of Ser. No. 32,398, Apr. 23, 1979, Pat. No. 4,228,150.

[51] Int. Cl.$^3$ .................. A61K 7/16; A61K 9/68; A61K 31/10; C07H 5/02
[52] U.S. Cl. ........................... 424/48; 424/49; 424/180; 426/3; 426/660; 536/122; 536/1.1; 536/18.7; 536/55
[58] Field of Search .............. 536/122, 1, 18; 424/48, 424/49, 180

[56] References Cited

U.S. PATENT DOCUMENTS

| | | | |
|---|---|---|---|
| 2,365,776 | 12/1944 | Raymond et al. | 536/122 X |
| 2,684,961 | 7/1954 | Barham | 536/122 |
| 2,927,058 | 3/1960 | Minto | 536/122 X |
| 4,228,150 | 10/1980 | Robyt et al. | 424/48 |

FOREIGN PATENT DOCUMENTS

| | | | |
|---|---|---|---|
| 9408 | 4/1980 | European Pat. Off. | 536/122 |
| 959407 | 6/1964 | United Kingdom . | |
| 1543167 | 3/1979 | United Kingdom | 536/122 |

OTHER PUBLICATIONS

Hough, L. et al., Nature, *London* (1976): 263(5580):800, "Enhancement in the Sweetness of Sucrose".
Drucker, D. B., J. Hum. Nutr., 1979 33(2), 114-124, Sweetening Agents in Food Drinks and Medicine Cariogenic Potential and Adverse Effects as Abstrin, Chem. Abstr. 91:3961D (1979).
Drucker, D. B., Arch. Oral. Biol., 1979, 24(12): 965-970, "Comparative Effects of the Substance Sweeteners Glucose Sorbitol Sucrose Xylitol and Trichlorosucrose on Lowering of pH by Two Oral S. Mutans Strains in Vitro", As Abstr. in Chem. Abstr. 93#8921q, 1980.
Jung Diss. Abstr. Int. B (1978), Alpha 1-Fluoroglucose as a Substrate for Dextran Sucrase.
Jung et al., Fed. Proc. 36(3) (1977):931, The Utilization of 1 Fluoro Glucose as a Substitute for Dextran Sucrase.
Anisuzzaman, et al., (1978), Carbohyd. Res. 61: 511-518.
Avigad, et al., (1956), Biochim, Biophys. Acta 20: 129-134.
Binkley, et al. (1979); Carbohyd. Res. 74: 337-340.
Bolton, et al. (1972), Carbohyd. Res. 21: 133-143.
Ganem, Bruce (1974), Tetrahedron Letters 1974 (11): 917-920.
Gibbons, et al. (1967), Arch. Oral Biol. 12: 11-24.
Gibbons, et al. (1968), Arch. Oral Biol. 13: 1249-1262.
Gibbons, et al. (1969), J. Bacteriol. 98: 341-346.
Khan, et al. (1980), Carbohyd. Res. 78: 185-189.
Lindley, et al. (1975), Carbohyd. Res. 43: 360-365.
Robyt, et al. (1974), Arch. Biochem. Biophys. 165: 634-640.
Scherp, Henry W. (1971), Science 173: 1199-1205.
Takeo, et al. (1974), Die Starke 26: 111-118.

*Primary Examiner*—Shep K. Rose

[57] ABSTRACT

Dextransucrase synthesis of dextran from sucrose is inhibited by substituted sucrose compounds which have an inhibiting group bonded to the 5-position ring carbon. Oral compositions containing such substituted sucrose compounds can be used to control dextran formation in the mouth, and dextran comprises the principal component of dental plaque.

14 Claims, No Drawings

METHOD OF INHIBITING DEXTRANSUCRASE AND ORAL COMPOSITIONS FOR USE THEREIN

GRANT REFERENCE

The invention described herein was made with the course of work under a grant from the Department of Health, Education, and Welfare, National Institute of Dental Research, Grant No. DE 03578.

CROSS-REFERENCE

This application is a continuation-in-part of co-pending application Ser. No. 32,398, filed Apr. 23, 1979, now U.S. Pat. No. 4,228,150.

BACKGROUND AND PRIOR ART

Dextrans are high molecular weight polysaccharides of D-glucopyranose units that are synthesized from sucrose by the enzyme dextransucrase. It is known that a number of bacterial species belonging to the family Lactobacilleae elaborate a dextransucrase enzyme. Ubiquitous species of such bacteria include *Leuconostoc mesenteroides, Streptococcus mutans,* and *Streptococcus sanguis.* These and similar bacteria form dextran as an extra-cellular slime. Dextran synthesizing bacteria are commonly present in the mouth, growing on the gums and teeth. The elaborated dextransucrase forms dextran from the sucrose passing through the mouth with foods or drinks, resulting in sticky deposits on the teeth.

The deposited dextran results in the formation of dental plaque, which holds aggregates of carious producing bacteria, and is known to be undesirable by contributing to caries and periodontal disease. Gibbons et al, *Arch. Oral Biol.,* 12:11 (1967); Gibbon et al, *Arch. Oral. Biol.,* 13:1249 (1968); Gibbons et al, *J. Bacteriol.,* 98:341 (1969); and Scherp, *Science,* 173:1199 (1971).

It is recognized that a means for decomposing dextran or impeding its synthesis in the mouth would be of benefit in controlling plaque formation, and, ultimately, in mitigating caries and periodontal disease. See Scherp, *Science,* 173:1199, at 1202 (1971). In this connection, it was suggested that dextranase might be employed to decompose dextran formed in the mouth. Even if this should prove feasible, a more fundamental approach is to inhibit dextran synthesis, thereby avoiding the formation of plaque. Heretofore, however, no method has been known for inhibiting or controlling the action of dextransucrase, except to reduce or withhold sucrose from the diet. This is not easy to accomplish. It is difficult to avoid oral intake of sucrose in countries such as the United States where it is present in a wide variety of foods and beverages. Moreover, sucrose is a natural constituent of many plant foods and, therefore, it would be expensive and impractical to completely eliminate it from normal diets.

The mechanism of action of dextransucrase has been described by Robyt et al, *Arch. Biochem. Biophys.,* 165:634 (1974). The mechanism postulates a glucosyl and a dextranosyl covalent enzyme intermediate. The glucose is obtained from sucrose and is incorporated into the growing dextran chain by a nucleophilic displacement of the $C_1$ of the reducing end of the dextranosyl chain by the $C_6$-hydroxyl of the glucosyl group forming a new α-1,6 glucosidic linkage.

SUMMARY OF THE INVENTION

This invention is based on the discovery that the replacement of the $C_6$-hydroxyl group of sucrose or the $C_5$-hydroxmethyl thereof by any of a wide variety of substituent groups results in inhibitory compounds which can be employed to prevent the dextransucrase synthesis of dextran from sucrose. While the mechanism of action is not known with certainty, it is probable that the substituted glucose unit of the inhibitory compound forms a covalent dead-end complex with dextransucrase, which blocks the action of the enzyme in the presence of sucrose.

Accordng to the mechanism proposed by Robyt et al (cited above), one of the reactions involves the nucleophilic attack by the $C_6$-hydroxyl oxygen of the covalently attached glucosyl unit onto the $C_1$ of the reducing end of the covalently attached dextran chain. The discovery of the inhibitory effect of the substituted sucroses of this invention is consistent with this theory.

The substituted sucrose which can be used in practicing the present invention includes compounds in which there is bonded to the 5-position ring carbon, or to both the 5-position and 5'-position ring carbons one of the following groups: $-CH_2X$, $=CH_2$, $-CHO$, or $-H$. The "X" of the $-CH_2X$ group can be $-Cl$, $-Br$, $-I$, $-N_3$, $-NH_2$, $-OCH_3$, or $-H$. For example the compound may be 6,6'-dideoxy-6,6'-dichloro, or -6,6'-dibromo, or -6,6'-diiodo, or-6,6'-diazido, or -6,6'-diamino sucrose.

The method of the present invention has utility for inhibiting the dextransucrase synthesis of dextran from sucrose. By introducing the substituted sucrose into the oral cavity the enzymes can be effectively inhibited. By this procedure, the biosynthesis of dextran can be controlled or prevented. Thus, by combining the substituted sucrose with a carrier suitable for use in the oral cavity, such as toothpaste, mouthwash, or chewing gum, an oral vehicle is provided for the control of plaque formation in the mouth. With certain of the substituted sucroses, the levansucrase synthesis of levan from sucrose is also inhibited. This is believed to be desirable in minimizing the formation of dental plaque, which also contain levan, although in relatively small amounts compared to its dextran content.

DETAILED DESCRIPTION

The structure of the substituted sucroses used in practicing the present invention can be made clear by considering the structure of the parent sucrose as represented below:

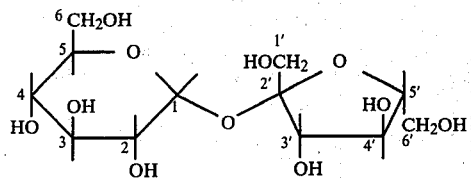

With reference to the above structured formula the critical substitution is for hydroxyl ($-OH$) group attached to the 6-position carbon or for the hydroxymethyl ($-CH_2OH$) attached to the 5-position carbon. A wide variety of substitutions in these positions will provide compounds of the desired inhibitory properties. In preparing such substituted sucroses, substitution by the same group will usually also occur with respect to the 6'-position or 5'-position carbons. The di-substituted compounds are therefore the preferred compounds for practicing the present invention. The following list of such substituted groups and the resulting compounds are illustrative:

| | Substitution for hydroxyl at 6 and 6' | | Sucrose Analogue Inhibitor |
|---|---|---|---|
| (1) | —Cl | (chloro) | 6,6'-dideoxy-6,6'-dichlorosucrose |
| (2) | —Br | (bromo) | 6,6'-dideoxy-6,6'-dibromosucrose |
| (3) | —I | (iodo) | 6,6'-dideoxy-6,6'-diiodosucrose |
| (4) | —N₃ | (azido) | 6,6'-dideoxy-6,6'-diazidosucrose |
| (5) | —NH₂ | (amino) | 6,6'-dideoxy-6,6'-diaminosucrose |
| (6) | —OCH₃ | (methoxy) | 6,6'-di-O-methylsucrose |
| (7) | —H | (hydrogen) | 6,6'-dideoxysucrose |
| (8) | ǀCH₂ | (methylene) | 5,6-5',6'-sucrose diene |
| (9) | —CHO | (aldo) | 6,6'-dialdo sucrose |
| (10) | —H | (hydrogen) | xylsucrose |

Summarizing, the substituted sucrose should have bonded to the 5-position ring carbon a group selected from —CH$_2$X, =CH$_2$ (methylene), —CHO, and —H. The "x" of the —CH$_2$X group may be —Cl, —Br, —I, —N$_3$, —NH$_2$, —OCH$_3$, or —H. Further, the same group which is bonded to the 5-position carbon may also be bonded to the 5'-position carbon. Preferred substitution groups are —CH$_2$Cl, —CH$_2$Br, and —CH$_2$I. For example preferred compounds include 6,6'-dideoxy-6,6'-dichlorosucrose, or dibromosucrose, or diiodosucrose.

The method of the present invention is practiced by introducing the inhibitor compound into an aqueous solution of dextransucrase. A sufficient amount of the inhibitor is dissolved to effectively form dead-end complexes with the enzyme and, thus prevent the synthesis of dextran from sucrose by dextransucrase. An inhibitory effect of the substituted sucroses can occur at concentrations as low as 5 milligrams of the inhibitor per milliliter of water. An effective concentration range for obtaining substantially total inhibition is usually from 50 milligrams to 100 milligrams per milliliter. Higher concentrations can be used although they are not required. In practical applications, concentrations of inhibitors in water greater than 100 mg. per ml. will usually not be employed, except that temporarily higher concentrations may be used in the mouth, depending on the mode of administration of the inhibitor.

For control of dextran formation in the oral cavity, it is preferred to apply the inhibitor in combination with a suitable carrier. The carrier may be water, a water solution of the inhibitor being prepared by the user as required. More desirably, however, the inhibitor may be dissolved in aqueous mouthwashes, which on use can serve the purposes of ordinary mouthwashes while providing the additional benefit of the dextran inhibition. Such aqueous solutions of aqueous mouthwashes can advantageously contain from 20 to 30 grams of the active substituted sucrose inhibitor per liter.

Other dental vehicles can be used for introducing the inhibitor into the mouth. These include toothpaste and toothpowders. Based on the weight of the toothpaste or toothpowder, it may advantageously contain from 1 to 5% by weight of the inhibitors based on the total weight of the toothpaste or toothpowder.

Other carriers suitable for use in the oral cavity can be employed. These include water-soluble tablets and chewing gum. A single tablet or single stick of chewing gum may contain from 1 to 5% by weight of the inhibitor. The term "tablet" as used here refers not only to tablets formed by pressure tableting, but also to cast or molded tablets, sometimes referred to as a lozenge, such as cough drops.

While some of the inhibitor will remain in the mouth after each treatment, such as each time the teeth are brushed or a mouthwash used, to provide the most effective control of dextran formation, repeated treatments at intervals of about 4 to 8 hours are desirable. For example, using an inhibitor-providing toothpaste or mouthwash in the morning, at supper time, and before bedtime, should provide reasonable effective control. For more frequent use, it may be convenient to employ the inhibitor in the form of tablets or chewing gum. These can advantageously be used at intervals of every 1 to 3 hours throughout the day, and can thereby provide even more effective control.

The method and preparation of this invention are further illustrated by the following examples.

EXAMPLE I 6,6'-dichloro-6,6'-dideoxysucrose (6,6'-dichlorosucrose) and 6,6'-dibromo-6,6'-dideoxysucrose (6,6'-dibromosucrose) were prepared using the methods of Anisuzzaman and Whistler, *Carb. Res.*, 61:511 (1978). Sucrose was reacted with triphenylphosphine and carbontetrachloride or carbontetrabromide in pyridine at 70° C. for 3 hrs. respectively to prepare the dichloro- or the dibromo-sucrose. The compounds were purified by silica gel column chromatography.

The precent inhibition of dextransucrase was determined by preincubating the enzyme 10 min. with 150 mM of the inhibitor. The enzyme was then assayed with $^{14}$C-sucrose, as described below.

| Inhibitor | % Inhibition |
|---|---|
| 6,6'-dichlorosucrose | 80 |
| 6,6'-dibromosucrose | 100 |

The enzyme was assayed by adding ½ volume of 0.3 M $^{14}$C-(U)-sucrose to the inhibitor-enzyme solution; equal aliquots were withdrawn with time and spotted onto 1.5×1.5 cm squares of Whatman 3 MM paper, which were immediately dropped into 20 ml anhydrous methanol. Three 200 ml volumes of methanol were added in 15 min. intervals. The papers were then removed, dried, and the radioactivity determined in a liquid scintillation spectrometer. The amount of radioactivity (polysaccharide formed) was plotted against the reaction time with sucrose (time of aliquot removed). The slopes of the resulting lines were determined and the percent inhibition calculated from the ratio of the slopes of the inhibited reactions to the slope of a control in which no inhibitor was added.

In further inhibition studies conducted as described above, the effect of different concentrations of the 6,6'-dibromosucrose inhibitor was studied. The results are summarized below:

| Inhibitor Concentration | % Inhibition |
|---|---|
| 5 mg/ml (11 mM) | 5 |
| 10 mg/ml (21 mM) | 12 |
| 25 mg/ml (53 mM) | 22 |
| 50 mg/ml (107 mM) | 66 |
| 70 mg/ml (150 mM) | 100 |

EXAMPLE II

Other inhibitor compounds for use in the methods and compositions of this invention can be prepared by known procedures, as follows:

6,6'-Diiodo-6,6'-Dideoxysucrose

This inhibitor can be prepared by refluxing 6,6'-dibromo-6,6'-dideoxysucrose (2 g) in dry butanone (100 ml) containing sodium iodide (1.5 g) for 30 hrs., or by selective iodination with triphenylphosphine and carbontetraiodide. See Anisuzzaman et al, *Carb. Res.*, 61:511 (1978).

6,6'-dideoxy-6,6'-diazidosucrose

This inhibitor can be prepared from the compounds of Examples I and II by treatment with sodium aside at 85° C. for 24 hrs. See Khan, et al, *Carb. Res.*, 78:185 (1980).

6,6'-Dideoxy-6,6'-Diaminosucrose

This inhibitor can be prepared from the corresponding diazidosucrose, described above, by hydrogenation in the presence of 5% palladium-on-barium sulfate at 80 p.s.i. for 6 hours at 40° C. see Kahn et al, cited above.

6,6'-di-O-Methylsucrose

This inhibitor can be prepared by detritylation of 6,6'-ditritylsucrose hexabenzoate, followed by methylation with diazomethane and borontrifluoride etherate and debenzoylation with sodium methoxide in methanol. See Lindley et al, *Carb. Res.*, 43:360 (1975).

6,6'-Dideoxysucrose

The inhibitor can be prepared by reacting 6,6'-diiodosucrose with four moles of sodium borohydride/mole of the diiodosucrose in dimethylsulfoxide at 60° C. for 8 hours. See Takeo, et al, *Starke*, 26:111 (1974). Alternatively the diiodosucrose can be irradiated in a solution of sodium hydrogen carbonate in 2-propanol under nitrogen with a 450 watt mercury-vapor lamp and a Corex filter. See Binkley, et al, *Carb. Res.*, 43:360 (1975).

5,6-5',6'-Sucrose Diene

The 6,6'-dibromosucrose or the 6,6'-diiodosucrose is benzoylated with benzoyl chloride and then treated with silver fluoride in pyridine for 28 hours at 22° C. to give the benzoylated diene. This is then debenzoylated with sodium methoxide in methanol. See Bolton, et al, *Carb. Res.*, 21:133 (1972) for preparation of benzoylated diene.

6,6'-Dialdo Sucrose 6,6'-dideoxy-6,6'dibromosucrose, (one mole) is treated with 2.2 moles of silver tetrafluoroborate in dimethylsulfoxide (5 mg/ml) for 8 hours at 22° C. to give this inhibitor. See Ganem, et al, *Tetrahedron Letters*, p. 917 (1974).

Xylsucrose

Xylsucrose can be synthesized from raffinose, xylose, and levansucrase. See Avigad, et al, *Biochem. Biophys. Acta.*, 20:129 (1956).

EXAMPLE III

In the following formulation examples, the inhibitor can be any of the inhibitors described above. The weight percents are on the basis of the pure (100%) inhibitor.

| Ingredients | % by wt. |
| --- | --- |
| Formula A | |
| Tooth Paste | |
| Glycerine | 19.95 |
| Carboxymethylcellulose | 1.14 |
| Sodium benzoate | 0.60 |
| Tetrasodium pyrophosphate | 0.35 |
| Dionized water | 20.63 |
| Dicalcium phosphate dihydrate | 46.38 |
| Calcium carbonate | 5.05 |
| Flavor | 0.90 |
| Inhibitor | 5.00 |
| Formula B | |
| Tooth Powder | |
| Magnesium silicate | 7.00 |
| Dicalcium phosphate dihydrate | 85.50 |
| Flavor | 2.50 |
| Inhibitor | 5.00 |
| Formula C | |
| Mouthwash | |
| Ethyl alcohol | 15.00 |
| Flavoring and coloring | 2.00 |
| Inhibitor | 5.00 |
| Deionized water | 78.00 |
| Formula D | |
| Chewing Gum | |
| Gum base | 92.00 |
| Corn syrup | 5.00 |
| Flavors and colors | 1.00 |
| Inhibitor | 2.00 |
| Formula E | |
| Tablet | |
| Mannitol | 94.00 |
| Flavor | 1.00 |
| Inhibitor | 5.00 |

We claim:

1. The method of inhibiting dextransucrase synthesis of dextran from sucrose, comprising introducing into an aqueous substrate containing sucrose and dextransucrase an inhibitory amount of a substituted sucrose compound, said substituted sucrose compound having bonded to the 5-position ring carbon a group selected from the class consisting of $-CH_2X$, $=CH_2$, $-CHO$, and $-H$, wherein X is selected from the class consisting of $-Br$, $-I$, $-N_3$, $-NH_2$, $-OCH_3$, and $-H$.

2. The method of claim 1 in which said group bonded to the 5-position ring carbon is $-CH_2I$.

3. The method of claim 1 in which said group bonded on the 5-position ring carbon is $-CH_2Br$.

4. The methods of claim 1 in which said substituted sucrose also has bonded to the 5'-position ring carbon the same group as bonded to the 5-position ring carbon.

5. The method of claim 1 in which said substituted sucrose is selected from the class consisting of 6,6'-dideoxy-6,6'-dibromosucrose, and 6,6'-dideoxy-6,6'-diiodosucrose.

6. An oral composition comprising a carrier suitable for use in the oral cavity containing an amount of a substituted sucrose compound effective for inhibiting the dextransucrase synthesis of dextran, said substituted sucrose compound having bonded to the 5-position ring carbon a group selected from the class consisting of $-CH_2X$, $=CH_2$, $-CHO$, and $-H$, wherein X is selected from the class consisting of $-Br$, $-I$, $-N_3$, $-NH_2$, $-OCH_3$, and $-H$.

7. The oral composition of claim 6 in which said group bonded to the 5-position ring carbon is —$CH_2I$.

8. The oral composition of claim 6 in which said group bonded to the 5-position ring carbon is —$CH_2Br$.

9. The oral composition of claim 5 in which said substituted sucrose also has bonded to the 5'-position ring carbon the same group as bonded to the 5-position ring carbon.

10. The oral composition of claim 5 in which said substituted sucrose is selected from the class consisting of 6,6'-dideoxy-6,6'-dibromosucrose, and 6,6'-dideoxy-6,6'-diiodosucrose.

11. The oral composition of claims 6, 7, 8, 9 or 10 in which said carrier is a toothpaste.

12. The oral composition of claims 6, 7, 8, 9 or 10 in which said carrier is a toothpowder.

13. The oral composition of claims 6, 7, 8, 9 or 10 in which said carrier is a chewing gum.

14. The oral composition of claims 6, 7, 8, 9 or 10 in which said carrier is a mouthwash.

* * * * *